US008214157B2

(12) United States Patent
Moser et al.

(10) Patent No.: US 8,214,157 B2
(45) Date of Patent: Jul. 3, 2012

(54) METHOD AND APPARATUS FOR REPRESENTING MULTIDIMENSIONAL DATA

(75) Inventors: Allan Robert Moser, Swarthmore, PA (US); Wade Thomas Rogers, West Chester, PA (US); Herbert Alan Holyst, Morton, PA (US)

(73) Assignee: Nodality, Inc., South San Francisco, CA (US)

( * ) Notice: Subject to any disclaimer, the term of this patent is extended or adjusted under 35 U.S.C. 154(b) by 637 days.

(21) Appl. No.: 12/293,081

(22) PCT Filed: Mar. 30, 2007

(86) PCT No.: PCT/US2007/008246
§ 371 (c)(1),
(2), (4) Date: Jun. 11, 2009

(87) PCT Pub. No.: WO2007/117423
PCT Pub. Date: Oct. 18, 2007

(65) Prior Publication Data
US 2009/0307248 A1 Dec. 10, 2009

Related U.S. Application Data

(60) Provisional application No. 60/787,908, filed on Mar. 31, 2006.

(51) Int. Cl.
*G01N 33/48* (2006.01)
*G01N 33/50* (2006.01)
(52) U.S. Cl. ............................... 702/19; 702/20
(58) Field of Classification Search .................. None
See application file for complete search history.

(56) References Cited

U.S. PATENT DOCUMENTS

| | | |
|---|---|---|
| 4,700,294 A | 10/1987 | Haynes |
| 4,845,653 A | 7/1989 | Conrad et al. |
| 4,987,539 A | 1/1991 | Moore et al. |
| 5,224,058 A | 6/1993 | Mickaels et al. |
| 5,627,040 A | 5/1997 | Bierre et al. |
| 5,701,256 A | 12/1997 | Marr et al. |
| 5,739,000 A | 4/1998 | Bierre et al. |
| 5,840,299 A | 11/1998 | Bendig et al. |
| 5,968,738 A | 10/1999 | Anderson et al. |
| 6,014,904 A | 1/2000 | Lock et al. |
| 6,178,382 B1 | 1/2001 | Roederer et al. |
| 6,495,333 B1 | 12/2002 | Willmann et al. |
| 6,535,672 B1 | 3/2003 | Paiam |
| 6,733,743 B2 | 5/2004 | Jordan |
| 6,944,338 B2 | 9/2005 | Lock et al. |
| 6,947,953 B2 | 9/2005 | Herzenberg et al. |
| 6,954,722 B2 | 10/2005 | Parks et al. |
| 7,321,843 B2 | 1/2008 | Orfao De Matos Correia E Vale et al. |
| 7,393,656 B2 | 7/2008 | Perez et al. |
| 7,650,351 B2 | 1/2010 | Herzenberg et al. |
| 7,734,557 B2 | 6/2010 | Meehan et al. |
| 2002/0029235 A1 | 3/2002 | Lock et al. |
| 2002/0049782 A1 | 4/2002 | Herzenberg et al. |
| 2003/0078703 A1 | 4/2003 | Potts et al. |
| 2003/0185436 A1 | 10/2003 | Smith |
| 2004/0143423 A1 | 7/2004 | Parks et al. |
| 2005/0044110 A1 | 2/2005 | Herzenberg et al. |
| 2005/0143928 A1 | 6/2005 | Moser et al. |
| 2005/0273475 A1 | 12/2005 | Herzenberg et al. |
| 2006/0015291 A1 | 1/2006 | Parks et al. |
| 2006/0046272 A1 | 3/2006 | Chow et al. |
| 2007/0078626 A1 | 4/2007 | Orfao De Matos Correia E Vale et al. |
| 2007/0299799 A1 | 12/2007 | Meehan et al. |
| 2009/0081699 A1 | 3/2009 | Perez et al. |
| 2009/0204557 A1 | 8/2009 | Zhang |
| 2009/0287421 A1 | 11/2009 | Malachowski et al. |
| 2009/0291458 A1 | 11/2009 | Cohen et al. |
| 2009/0327240 A1 | 12/2009 | Meehan et al. |
| 2010/0070459 A1 | 3/2010 | Zigon et al. |
| 2010/0070502 A1 | 3/2010 | Zigon |
| 2010/0070904 A1 | 3/2010 | Zigon et al. |
| 2010/0086951 A1 | 4/2010 | Hedley et al. |
| 2010/0161561 A1 | 6/2010 | Moore et al. |
| 2010/0228491 A1 | 9/2010 | Gutierrez et al. |
| 2010/0240542 A1 | 9/2010 | Soper et al. |

FOREIGN PATENT DOCUMENTS

| | | |
|---|---|---|
| WO | WO 03/067210 A2 | 8/2003 |
| WO | WO 03/067210 A3 | 12/2003 |
| WO | WO 2006/012507 A2 | 2/2006 |
| WO | WO 2006/012507 A3 | 10/2006 |
| WO | WO 2009/025847 A2 | 2/2009 |
| WO | WO 2009/025847 A3 | 6/2009 |
| WO | WO 2010/006291 A1 | 1/2010 |
| WO | WO 2010/028277 A1 | 3/2010 |
| WO | WO 2010/045651 A1 | 4/2010 |
| WO | WO 2010/135608 A1 | 11/2010 |

OTHER PUBLICATIONS

Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

Crans-Vargas, et al. CREB as a prognostic marker in acute leukemia. Abstract. Blood. 2001; 98(11), part 1, p. 316a.

European search report and search opinion dated Feb. 22, 2011 for Application No. 10180167.8.

Irish, et al. Single cell profiling of potentiated phospho-protein networks in cancer cells. Cell. Jul. 23, 2004;118(2):217-28.

(Continued)

*Primary Examiner* — Jason Sims
(74) *Attorney, Agent, or Firm* — Wilson Sonsini Goodrich & Rosati

(57) ABSTRACT

The present invention relates to methods for representing multidimensional data. The methods of the present invention are well suited but not limited to the representation of multidimensional data in such a way as to enable the comparison and differentiation of data sets. For example, the invention may be applied to the representation of flow cytometric data. The invention further relates to a program storage device having instructions for controlling a computer system to perform the methods, and to a program storage device containing data structures used in the practice of the methods.

17 Claims, 7 Drawing Sheets

OTHER PUBLICATIONS

Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.

Kornblau, et al. Dynamic single-cell network profiles in acute myelogenous leukemia are associated with patient response to standard induction therapy. Clin Cancer Res. Jul. 15, 2010;16(14):3721-33. (abstract).

Krutzik, et al. Analysis of protein phosphorylation and cellular signaling events by flow cytometry: techniques and clinical applications. Clinical Immunology. 2004; 110: 206-21.

Marvin et al. Normal bone marrow signal transduction profiles: a requisite for enhanced detection of signaling dysregulations in AML. Blood. Jan. 13, 2011.doi:10.1182/blood-2010-10-316026 [Epub ahead of print].

Perez, et al. LFA-1 signaling through p44/42 is coupled to perforin degranulation in CD56+CD8+ natural killer cells. Blood. Aug. 15, 2004;104(4):1083-93.

Perez, et al. Simultaneous measurement of multiple active kinase states using polychromatic flow cytometry. Nat Biotechnol. 2002; 20: 155-62.

Rosen, et al. Functional characterization of FLT3 receptor signaling deregulation in acute myeloid leukemia by single cell network profiling (SCNP). PLoS One. Oct. 27, 2010;5(10):e13543.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005;7(4):351-62.

Spiekermann, et al. Overexpression and constitutive activation of FLT3 induces STAT5 activation in primary acute myeloid leukemia blast cells. Clinical Cancer Research. Jun. 2003; 9:2140-2150.

UK office action and search report dated Feb. 22, 2011 for GB Application No. 1017857.2.

Zheng, et al. Regulation of STAT3 and STAT5 in the differentiation of FLT3/ITD expressing 32Dc13 cells induced by G-CSF and CEP-701. Abstract 2935.Blood. 2002; 100(11) and 44th Annual Meeting of the American Society of Hematology. Philadelphia, PA, USA. Dec. 6-10, 2002.

Jennings, et al. Recent advances in flow cytometry: application to the diagnosis of hematologic malignancy. Blood. Oct. 15, 1997;90(8):2863-92.

Roederer, et al. Probability binning comparison: a metric for quantitating multivariate distribution differences. Cytometry. Sep. 1, 2001;45(1):47-55.

Adam et al., "Serum Protein Fingerprinting Coupled with a Pattern-matching Algorithm Distinguishes Prostate Cancer from Benign Prostate Hyperplasia and Healthy Men", Cancer Res. 62:3609-3614 (2002).

Conrads et al., "High-resolution Serum Proteomic Features for Ovarian Cancer Detection", Endocrine-Related Cancer 11:163-178 (2004).

Daly et al., "High-resolution Haplotype Structure in the Human Genome", Nat. Genet. 29:229-32 (2001).

Li et al., "Proteomics and Bioinformatics Approaches for Identification of Serum Biomarkers to Detect Breast Cancer", Clin. Chem. 48:1296-1304 (2002).

Petricoin et al., "Use of Proteomic Patterns in Serum to Identify Ovarian Cancer", Lancet. 359:572-577 (2002).

Valerio et al., "Serum Protein Profiles of Patients with Pancreatic Cancer and Chronic Pancreatitis: Searching for a Diagnostic Protein Pattern", Rapid Commun. Mass. Spectro. 15:2420-2425 ( 2001).

Wright et al., "Proteinchip Surface Enhanced Laser Desorption Ionization (SELDI) Mass Spectrometry: A Novel Protein Biochip Technology for Detection of Prostate Cancer Biomarkers in Complex Protein Mixtures", Prostate Cancer Prostatic. Dis. 2:264-276 (1999).

Benekli, et al. Signal transducer and activator of transcription proteins in leukemias. Blood. Apr. 15, 2003;101(8):2940-54.

Birkenkamp, et al. Regulation of constitutive STAT5 phosphorylation in acute myeloid leukemia blasts. Leukemia. 2001; 15(12):1923-31.

Chow, et al. Constitutive phosphorylation of the S6 ribosomal protein via mTOR and ERK signaling in the peripheral blasts of acute leukemia patients. Experimental hematology. 2006; 34(9):1182-1190.

METHOD AND APPARATUS FOR REPRESENTING MULTIDIMENSIONAL DATA

CROSS-REFERENCE TO RELATED APPLICATIONS

This is a National Stage application of PCT International Application No. PCT/US2007/008246, filed Mar. 30, 2007, which in turn claims the benefit of U.S. Provisional Application No. 60/787,908, filed on Mar. 31, 2006 each of which is hereby incorporated by reference in its entirety herein.

BACKGROUND OF THE INVENTION

A common task for many applications is to compare data sets in order to distinguish two or more classes forming subpopulations of those data. One example of such an application involves the use of flow cytometry for medical diagnosis.

Flow cytometry can be used to measure properties related to individual cells in a sample of blood drawn from a patient. A liquid stream in the cytometer carries and aligns individual cells so that they pass through a laser beam in single file. As a cell passes through the laser beam, light is scattered from the cell surface. Photomultiplier tubes collect the light scattered in the forward and side directions which gives information related to the cell size and shape. This information may be used to identify the general type of cell (e.g. monocyte, lymphocyte, granulocyte.)

Additionally, fluorescent molecules (fluorophores) that can be conjugated with antibodies can be activated by the laser and emit light. Since these antibodies bind with antigens on the cells, the amount of light detected from the fluorophores is related to the number of antigens on the surface of the cell passing through the beam. The specific set of fluorescently tagged antibodies that is chosen can depend on the types of cells to be studied since different types of cells have different distributions of cell surface antigens. Several tagged antibodies are used simultaneously, so measurements made as one cell passes through the laser beam consist of scattered light intensities as well as light intensities from each of the fluorophores. Thus, the characterization of a single cell can consist of a set of measured light intensities that may be represented as a coordinate position in a multidimensional space. Considering only the light from the fluorophores, there is one coordinate axis corresponding to each of the fluorescently tagged antibodies. The number of coordinate axes (the dimension of the space) is the number of fluorophores used. Modern flow cytometers can measure several colors associated with different fluorophores and thousands of cells per second. Thus, the data from one subject can be described by a collection of measurements related to the number of antigens of certain types on individual cells for each of (typically) many thousands of individual cells.

By way of example, one would like to determine if a patient has a specific illness based on a set of objective measurements obtained from a blood sample that is analyzed with a flow cytometer. The terminology used to describe data is as follows. One case (e.g. the flow cytometric data derived from a blood sample taken from a patient) is called a "sample instance." (The terms "instance" and "sample" are also used.) Several sample instances may be associated with each other forming a class of instances such as the class of patients having a disease or the class of patients who are healthy. Multiple sets of measurements (e.g. the measured light intensities for each cell passing through the flow cytometer) can be made for one instance. Each of these sets of measurements can be referred to as an "event." In terminology of the present invention, the data for an instance can consist of a distribution of points in a multidimensional space, with each point representing one event and with each coordinate of a point representing a measurement of light intensity from a single fluorophore. For example, FIG. 1 shows an example of flow cytometry data for four fluorescent parameters. Since humans cannot visualize a 4-dimensional space, these data are shown as pair-wise dot plots.

Data of the type described above, consisting of several thousand events (or points) in a multidimensional parameter space, is best described as a density function, i.e. the number of events contained in a volume of space. Often, this density function is normalized by the total number of events comprising the instance. If this density function is known for some population of instances, it can be used to specify the probability than an event will be found within some region of the parameter space for instances belonging to this population. In mathematical terminology this is referred to as a probability density function (PDF).

In the example of flow cytometry for medical diagnosis, each class of instances (e.g. diseased or healthy) has an associated multidimensional PDF. The problem that arises in diagnosis can be that of determining the PDF for two or more classes of instances, measuring the density of events for a newly observed instance, and by comparing these distributions, assigning the newly observed instance to a class. Thus, accurately representing multidimensional data in such a way as to enable this classification is critical.

Flow cytometry has been in use as a clinical tool for many years (Johnson 1993 and Jennings 1997). In many applications, an optimized panel of antibodies is used to identify specific cell types. If a cell of a specific type is present, the intensity measured for the corresponding fluorophore will be high (positive events); if it is not present, the intensity will be low (negative events). In this case, one can count cells of different types by applying a threshold to the signal such that the signal intensity for negative events falls below the threshold and the signal intensity for positive events falls above the threshold. For multiple antibodies, the flow cytometric space is divided into "quadrants" using these thresholds, and thus the numbers of cells in each quadrant can be counted.

An example is shown in FIG. 2 for T-lymphocytes. CD4 positive events indicate the presence of helper T cells that play a role in regulating immune response. CD8 positive events indicate the presence of cytotoxic T cells that destroy infected cells. The ratio of CD4 positives to CD8 positives is a measure of immune status and can be used to diagnose or follow the progression of HIV infection since the HIV virus targets helper T cells.

Flow cytometric quadrant analyses, as described above, are possible when the cell antigens and specific antibodies are well characterized. However, in cases where these are not known or cell surface markers change with time, the distributions of intensity levels from flow cytometry measurements are complex and thus a simple positive/negative analysis is not possible. An example of an especially important class of cells that are not well characterized is Circulating Endothelial Progenitor Cells (CEPCs). These cells play a key role in post-natal angiogenesis and vascular development. A method of cytometrically identifying CEPCs would be of great interest for diagnostics and therapeutics related to cardiovascular pathology and conditions involving neovascularization such as ischemia, diabetic retinopathy, and tumor growth.

Other methods of representing and analyzing multidimensional flow cytometry data have been developed. One that is most closely related to the herein described methods and apparatus is Probability Binning (Roederer 2001). Roederer's method of Probability Binning represents a multidimensional probability distribution as a set of bins defining regions of the multidimensional space. The boundaries of these bins are chosen so that approximately equal numbers of events lie in each bin. Bins are found recursively by selecting a coordinate dimension, determining the median in that coordinate, and subdividing the data such that events whose values for this coordinate are less than the median are placed in one bin while those whose values for this coordinate are greater than the median are placed in another bin. Dividing the data at the median insures that for each subdivision of a "parent" bin, the "children" bins have equal numbers of events (plus or minus one if the number of events in the parent bin is odd). These two children bins are then processed in a similar way, splitting the data into four bins. This recursive method is continued until the desired number of bins is obtained. The method used by Roederer et. al. to select the coordinate dimension at each subdivision is to calculate the variance of the data in the parent bin for all the coordinate dimensions and choose the dimension having the largest variance. It is important to note that this split always occurs on one of the coordinate axes of the data as originally presented. Thus, if the space is 4-dimensional, the data will be divided according to the coordinate corresponding to one of those four dimensions. Although the decision is made on the basis of the variance in each dimension, the split is not necessarily along the optimal direction since the direction of maximum variance may not coincide with one of the coordinate axes.

However, current practices and approaches fall short of providing efficient, robust, reliable and accurate systems of representing multidimensional data that can be used to address the herein discussed problems. From the foregoing, it is appreciated that there exists a need for methods and an apparatus that overcome the shortcomings of those existing previously.

BRIEF SUMMARY OF THE INVENTION

In an illustrative implementation, the herein described apparatus and method can use a method similar to probability binning (referred to herein as Equal Probability Binning). In an illustrative implementation, the method utilized can form bins by splitting data in the direction of maximum variance rather than along an original coordinate axis. In an illustrative implementation, the direction of maximum variance can be first determined and then the data space can be rotated such that the principle coordinate axis lies in the direction of maximum variance. Second, a hierarchical, multiresolution representation of the data can be created. This can be done by retaining and utilizing information for bins at each level of recursion. The binned data can be used to develop a fingerprint that can be a one-dimensional representation embodying the information contained in the multiresolution, multidimensional representation. Additionally, the herein described apparatus and methods can include novel algorithms for finding and representing bins from one data set and utilizing the bin representation to process a second data set. It can also include a novel method of forming a differential fingerprint that represents the degree of dissimilarity of a given instance to two or more classes of instances.

BRIEF DESCRIPTION OF THE DRAWINGS

The invention will be more fully understood from the following detailed description, taken in connection with the accompanying drawings, which form a part of this application and in which.

DETAILED DESCRIPTION

Figure 1:
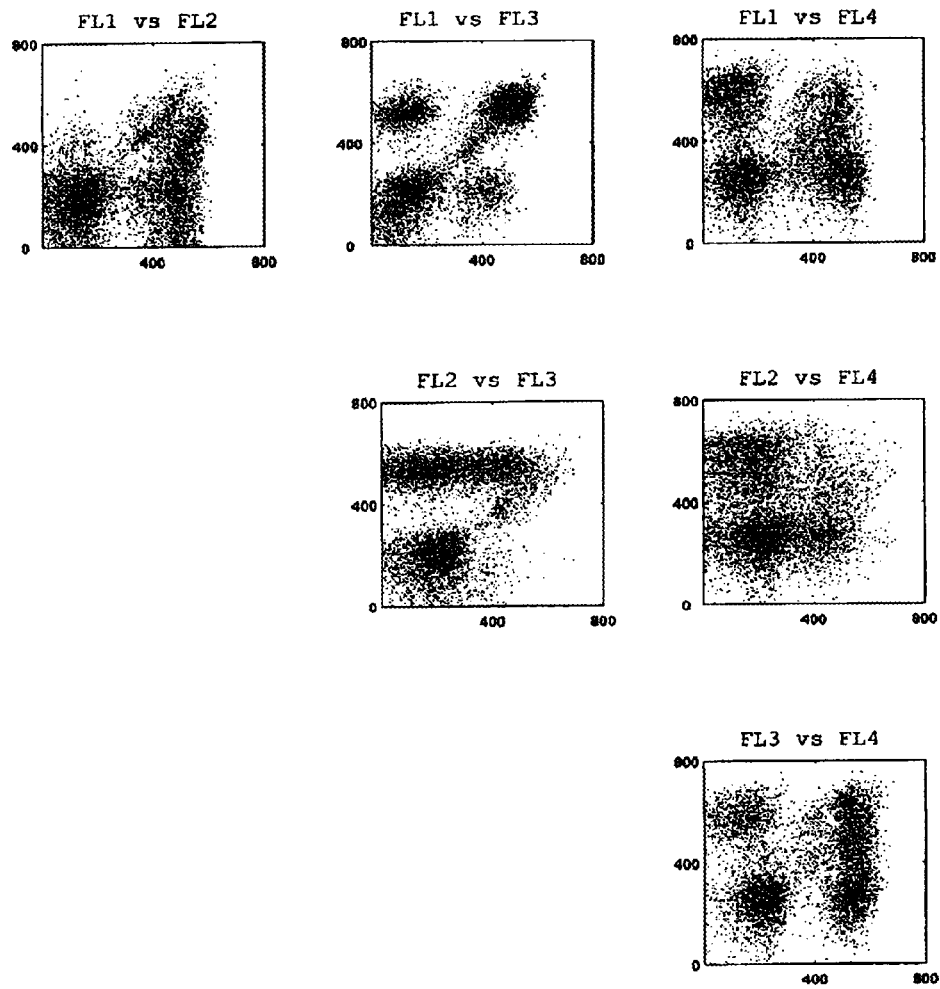
FIG. 1 shows an example of a 4-dimensional data set taken from flow cytometry. Since a 4-dimensional space cannot be visually displayed, these data are shown as pair-wise dot plots.

The problems stated in the Background section above, and in particular, the problems of the prior art, are solved by the herein-described method and apparatus for representing distributions of multidimensional data by a set of regions (referred to as bins). A novel form of binning, the method for which is disclosed herein called Multidimensional Minimum Variance Equal Probability Hierarchical Binning, is used in conjunction with other data-mining and statistical analysis tools to compare distributions and, for example, classify sets of samples by determining whether their distributions vary significantly.

The bins in this representation partition the space into discrete regions that may be enumerated. That is, each bin is assigned a unique number. This enumeration enables the representation of the multidimensional probability density in the form of a linear sequence of numbers referred to herein as a "fingerprint." Given a set of instances, each originally described by a collection of points in a multidimensional space, each instance from this set may be processed as described by this invention to form a fingerprint representing the probability density information for that instance. These fingerprints may then be used in a variety of subsequent data analysis applications. A particular example of such an analysis is to discover patterns among the collection of instances where a pattern in this context is defined as a specific combination of fingerprint features.

In one embodiment, the herein described apparatus and method feature a program storage device readable by a machine, the program storage device tangibly embodying a program of instructions executable by a machine to perform a method for representing multidimensional data. The method includes defining a subdivision of the data into a discrete set of bins such that the probability density function (PDF) for the data is approximated by this set of bins. Each bin is described by a bounding set of intersecting hyperplanes in the space defined by the set of parameters of the multidimensional data. Every bin in this representation describes a region of equal probability. Thus, the PDF for the multidimensional data is approximated by the collection of bins and the hyperplane boundaries defining each bin.

In another embodiment, the herein described apparatus and method include a procedure for forming a set of hierarchical bins such that the PDF for the multidimensional data is represented at multiple resolutions. A single bin, whose hyperplane boundaries enclose all of the data, represents the PDF at the coarsest resolution. The next level of resolution is obtained by subdividing this single bin thereby obtaining two bins. Successively finer resolution representations are obtained by iteratively subdividing each bin of the previous level of resolution. The totality of all bins at all levels of resolution and their hyperplane boundaries thus defines a multiresolution representation of the PDF.

In another embodiment, the herein described apparatus and method include a procedure for representing the PDF wherein the collection of bins described above approximate the PDF for the multidimensional data in such a way that the variance of data values within each bin is optimally reduced at each subdivision into finer resolution bins. This is accomplished by rotating the coordinate axes such that one axis is in the direction of maximum variance. The subdivision of the bin is made along this direction at the median value thereby reducing the variance by the largest amount compatible with the constraint of maintaining an equal number of samples within each bin.

In another embodiment, the herein described apparatus and method include a procedure for utilizing the bin representation of one data set, found through Multidimensional Minimum Variance Equal Probability Hierarchical Binning, to bin data from a second data set. Thus, one data set, found for example by aggregating many samples, may be utilized to find a template for binning other samples. This is particularly useful for detecting differences between individual samples' PDFs.

In another embodiment, the herein described apparatus and method include a procedure to enumerate the bins such that the PDF for multidimensional data is represented as a linear sequence of features referred to as a fingerprint. The features comprising this sequence are the continuous-valued numbers for event densities listed in the order of their corresponding enumerated bin. The features of these fingerprints may be transformed by mathematical operations. Examples of such transformations include but are not limited to taking the logarithm of the numbers, performing linear transformations of these numbers, or combining these or similar operations. The event density fingerprints and any continuous-valued mathematical transformation of them are referred to as "continuous-valued fingerprints." The features of continuous-valued fingerprints may further be transformed in a manner that produces categorical features. Categorical features have a discrete number of possibilities, such as integers (e.g. "1", "2", "3"), alphabetic symbols (e.g. "a", "b", "c"), or textual labels (e.g. "high", "medium", "low"). These fingerprints are referred to as "categorical fingerprints." The features of categorical fingerprints may be further processed to represent each feature by a string of binary features (1's and 0's). These binary representations are referred to as "binary fingerprints."

DETAILED DESCRIPTION OF THE INVENTION

For data comprised of multiple measurements for multiple parameters, the distribution of events in said data can be described by a density function in a multidimensional space. A method is disclosed for representing this multidimensional data as a set of regions referred to as bins; each bin enclosing a discrete region of the data space having equal numbers of events. Further, a method is disclosed for representing said data in a hierarchical fashion creating a multiple resolution representation in which each bin at a given resolution has two sub-bins encompassing the same region such that the sub-bins represent the data at the next higher level in the resolution hierarchy. Further, a method is disclosed for forming said bins such that at each subdivision of a bin at one resolution into two bins of higher resolution, the subdivision is made by a boundary that maximally reduces the variance of the data within the bin. A method is also disclosed for representing the information describing bins found by the above methods for one data set and using this information to efficiently determine bin membership of events derived from another source of data. A method is also disclosed for forming a one-dimensional fingerprint representation of the multiresolution, multidimensional data. Additionally, a method is disclosed for forming differential fingerprints that efficiently represent differences between data sets from two or more classes of data.

A computer readable medium having instructions for controlling a computer system to perform the method and a computer readable medium containing a data structure used in the practice of the method are also disclosed.

In an embodiment of the invention, the first step in representing the distribution of multidimensional data is to specify the number of hierarchical levels (L) for the representation. Successive hierarchical levels represent the space at successively finer resolutions. The total number of bins ($N_T$) into which the space is to be divided is related to the number of hierarchies by: $N_T = 2^L - 1$. For, example, if the number of desired hierarchies is 9, the total number of bins will be 511. The number of bins at each resolution level, k, is: $n_r = 2^k$ where $k = 0, 1, \ldots, L-1$. Thus, the first resolution level, $k=0$, consists of one bin which encompasses the entire range of parameters defining the space in which the data exist. The second resolution level, k=1, consists of two bins dividing the space into two regions. The third level, k=2, consists of four bins, and so on. The number of bins at each resolution level for nine hierarchies is summarized in the following table.

| Hierarchy | Resolution Level | Number of bins |
|---|---|---|
| 1 | 0 | 1 |
| 2 | 1 | 2 |
| 3 | 2 | 4 |
| 4 | 3 | 8 |
| 5 | 4 | 16 |
| 6 | 5 | 32 |
| 7 | 6 | 64 |
| 8 | 7 | 128 |
| 9 | 8 | 256 |

Typically, one would determine the number of finest resolution bins first, requiring some minimum number of events to be in each bin. By way of a non-limiting example, if the total number of events is 10,000 and approximately 40 events are required to be in each bin at the finest resolution, the resulting number of high resolution bins would be 250. The closest power of two is 8 ($2^8$=256), and thus L=9 would be specified as the number of resolution levels resulting in a total of 511 bins.

The next step in this procedure is to determine bin boundaries that subdivide the multidimensional space into regions of equal probability. This is done in a recursive fashion such that a hierarchical set of bin boundaries are found that first subdivide the space into two regions, next into four regions, and so on until the desired resolution is obtained. Additionally, the subdivision of the space is done in such a way that at each division of a parent bin into two child bins, the parent bin is divided by a hyperplane perpendicular to the direction of maximum variance of data within the bin. Thus, the variance of data within a bin is maximally reduced at each subdivision. A method known as Principle Components Analysis (PCA) may be utilized to find the direction of maximum variance (O'Connel 1974). Other methods will be understood by the skilled artisan armed with the present disclosure.

Method for Finding Bin Boundaries

In an embodiment of the invention, the method for finding the bin boundaries for a given data set is described as follows.

Description of Data:

A data set D, consisting of m sets of events x, each consisting of p values is described by the set of points:

$$X^j=(x^j_1, x^j_2, \ldots, x^j_p), \text{ where } j=1, 2, \ldots, m$$

and each $x^j_i$ is a number.

Figure 3:
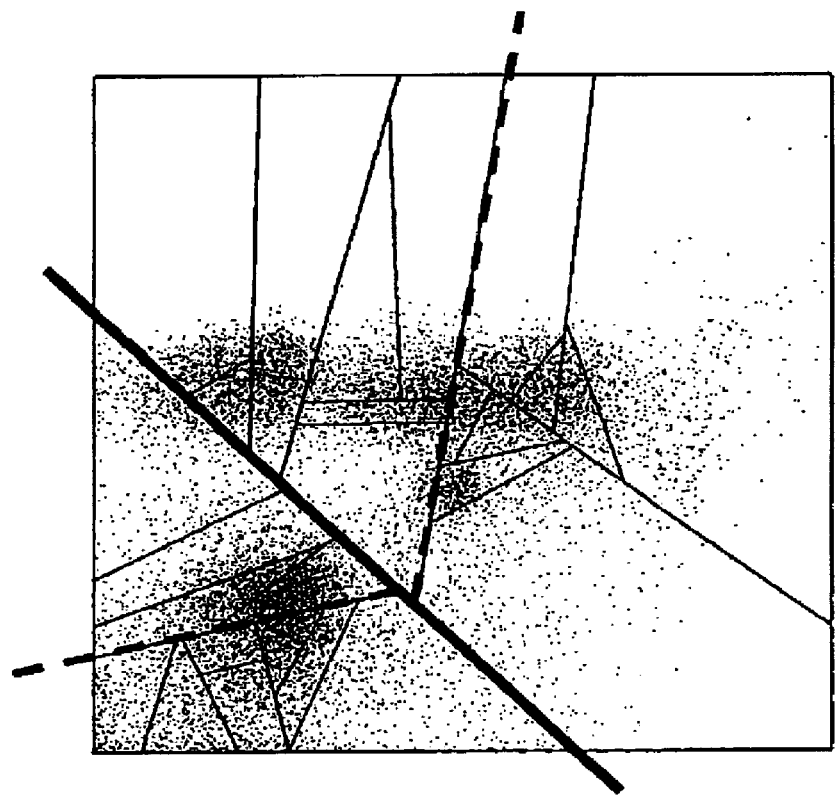
FIG. 3 shows an example of the result of minimum variance, equal probability, hierarchical binning for a 2-dimensional data set from flow cytometry data. The rectangular box enclosing the entire data set is the resolution level 0 bin. The first subdivision of the data is shown by the heavy solid line which divides the level 0 bin into two equally populated children bins. This line is in the direction of maximum variance for the entire data set. The two children bins form the resolution level 1 representation. The two bins at resolution level 1 are each divided into two bins as indicated by the heavy dashed lines. Again, the dashed lines are in the direction of maximum variance for the subspaces being divided. The 4 bins resulting from this subdivision form the resolution level 2 representation of the data. This procedure is carried out recursively for levels 2 3, and 4. At each step in the recursion, the number of bins is doubled to form the next resolution level in the resolution hierarchy. The final resolution level is 5, having a total of 32 bins.

These data may be represented as points in a p-dimensional space. For example, points in a 2-dimensional space consist of pairs of numbers, points in a 3-dimensional space are triplets of numbers, and so forth. A graphical example of a 2-dimensional space from flow cytometry data is shown in FIG. 3.

Method:

In one aspect, the bin determination procedure is described in steps (1) through (3) below. Step (1) initializes the binning procedure, setting values for the lowest resolution bin which encompasses the entire set of data points. Step (2) describes a loop which successively subdivides the data space into finer resolution bins. This step has subparts that loop over the bin resolution levels. Step (3) terminates the binning procedure.

The steps are as follows:
(1) Initialization
   a. For each dimension, i where i=1, 2, . . . , p, in the p-dimensional space, find the minimum ($xmin_i$) and maximum ($xmax_i$) data values:
      [($xmin_1$, $xmax_1$); ($xmin_2$, $xmax_2$); . . . ; ($xmin_p$, $xmax_p$)].
   b. The set of 2p hyperplanes defined by:

$$x_1=xmin_1, x_1=xmax_1,$$

$$x_2=xmin_2, x_2=xmax_2,$$

$$\ldots$$

$$x_p=xmin_p, x_p=xmax_p$$

form a boundary enclosing the entire data space and define the zero'th resolution level bin. These boundaries are stored for future use.
   c. Set two bin counters, $n_{beg}$ and $n_{end}$, which define the beginning and ending bin numbers for the current resolution level. For the zero'th resolution level, set k=0, $n_{beg}$=1, and $n_{end}$=1.
   d. Set a bin counter, b, to b=1.
      (This counter will be incremented as additional bins are formed at higher resolutions.)
   e. Store the data contained within the boundaries of the current bin in an array, $D_1$=D. The number of data points in $D_1$, is $m_1$=m.
(2) Begin a loop over bins using b as a bin number counter. Continue this loop until the value of b exceeds $N_T$. When b exceeds $N_T$, continue at step (3) below
   a. Increment the resolution level, k=k+1, and set n=$n_{beg}$.
   b. Begin a loop over bins, n=$n_{beg}$ to $n_{end}$.
      i. Find the direction of maximum variance of the data contained within bin n by PCA. This is done in two steps. First, find the covariance matrix for the data contained within bin n. Next, perform a Singular Value Decomposition (SVD) on the covariance matrix. (For a description of SVD see, for example, Golub 1996.) As is known by those skilled in the art, this procedure finds the rotation matrix that can be used to rotate the coordinates of the data space such that the first dimension of the rotated space is along the direction of maximum variance.
      The rotation matrix found in this step is denoted, $R_n$.
      ii. Rotate the $m_n$ data points, $D_n$, contained within bin n by the rotation matrix found in the preceding step. Since $D_n$ can be represented in the form of a matrix, this is accomplished through matrix multiplication. The rotated data is referred to as $D_n'$ and has points described by: $x'=(x'_1, x'_2, \ldots, x'_p)$.
      Because of the rotation performed in this step, the values of the first component, $x'_1$, are measured relative to the direction of maximum variance.
      iii. Find the median value for $x'_1$ from the $m_n$ data points contained in $D_n'$. The median value may be found by ranking the values of $x'_1$ for all data points and storing them in a list. The middle value in this list is the median and is referred to as the "split" value, $x_{split}$. Set $t_n=x_{split}$.
      iv. For the current bin, n, save the values of the data array, $D_n'$, the split value, $t_n$, and the rotation matrix, $R_n$, which will be used in the next iteration of the loop. Also, record the values of $t_n$ and $R_n$ to an output storage device. (These values will be used in the procedure to find the bins into which data points from new data sets are distributed.)

v. Divide the data points in bin n according to whether their values for $x'_1$ are less than or greater than $t_n$. The split data is stored in two arrays:

$D_{low}$ contains points, j, such that the values $x^{ij}_1$ are less than or equal to $t_n$.

$D_{high}$ contains points, j, such that the values $x^{ij}_1$ are greater than $t_n$. Since the data is split at the median value, half of the data is stored in $D_{low}$ while the other half of the data is stored in $D_{high}$. (If there are an odd number of points in the un-split data set, $D_{low}$ will contain one more point than the number in $D_{high}$).

Note that the data stored in these two arrays remain in the rotated coordinate system.

vi. Increment the bin counter, b, by one: b=b+1, and store the data points, $D_{low}$, in bin b:

$D_b = D_{low}$.

(This bin is the next higher resolution level containing data points whose first coordinate in the rotated system fell below the median.)

vii. Increment the bin counter, b, by one: b=b+1, and store the data points, $D_{high}$, in bin b:

$D_b = D_{high}$.

(This bin is the next higher resolution level containing data points whose first coordinate in the rotated system fell above the median.)

viii. Increment counter n: n=n+1

If n is less than or equal to $n_{end}$, continue the loop over n at step (2)b.

Otherwise, proceed with step (2)c.

c. Replace the current values of $n_{beg}$ and $n_{end}$ as follows:

$n_{beg} = n_{end}+1$, and $n_{end} = b$.

(These new values of $n_{beg}$ and $n_{end}$ will form the range of bins for the next resolution level.)

d. Continue the loop which began at step (2) above.

(3) Terminate the binning procedure.

By way of a non-limiting example of the binning procedure described above, consider forming 15 bins. Thus, $N_T = 15$ and the number of hierarchical resolution levels is 4, labeled by k=0, 1, 2, 3. Step (1) forms resolution level 0 which consists of the entire space within which the data points are contained. Step (2) begins with bin b=1 (the level 0 resolution bin). The loop beginning at step (2)b is executed 3 times with:

n=1 to 1 (loop over resolution level 0)
n=2 to 3 (loop over resolution level 1)
n=4 to 7 (loop over resolution level 2).

The first loop finds the direction of maximum variance for the entire set of data points and splits the data into two equal portions. This procedure forms bins 2 and 3 which each contain one-half of the data points. The next pass through the loop at step (2)b uses the values in bins 2 and 3. First, it finds the direction of maximum variance for the data in bin 2 and splits these data into two equal portions that form bins 4 and 5. Next, it finds the direction of maximum variance for the data in bin 3 and splits these data into two equal portions that form bins 6 and 7. The final pass through loop (2)b uses the values in bins 4 through 7. It first finds the direction of maximum variance for the data in bin 4 and splits these data into two equal portions that form bins 8 and 9. Next, it processes the data in bin 5, again finding the direction of maximum variance for these data and splits these data into two equal portions that form bins 10 and 11. Continuing with bin 6, the direction of maximum variance is found and the two higher resolution bins 12 and 13 are determined. Finally, the data in bin 7 are utilized following the same procedure to split these data into two equal portions along the direction of maximum variance forming bins 14 and 15. At each step, the information for the rotation matrices and split values are recorded. As will be demonstrated in a following section, these recorded parameters may be used to process a new dataset, partitioning points from these new data into the regions found in the binning procedure.

It is noteworthy that while the bin boundaries consist of the intersection of hyperplanes in a p-dimensional space, these boundaries do not need to be explicitly stored. All of the information necessary to bin new data is contained in the rotation matrices and split values. This will be demonstrated in the procedure described below for binning a new data set. Thus, the representation of a multidimensional data space by this binning procedure is embodied in the rotation matrices and split values. The hyperplane bin boundaries may be extracted from the rotation matrices and split values. Starting from the set of hyperplanes bounding all of the data stored in step (1)b, the rotation matrix describing the first subdivision of the space can be used to find the direction in which the data was split. The bin boundaries for the two bins into which the data was split may be found by intersecting the hyperplane perpendicular to this direction with the hyperplanes bounding the entire data space. Bin boundaries for successively finer resolution bins may be found by multiplying the successive rotation matrices, finding the direction in which a bin was split, and intersecting the hyperplane perpendicular to this direction with the boundaries of the bin.

A non-limiting example of this binning procedure is shown in FIG. 3. The dimensionality of the space for this example is two so that the results can be graphically displayed.

Method for Binning a New Data Set

In one embodiment of the invention, events from a new data set $D_{new}$, can be assigned to bins determined from another data set $D_{old}$, found by the method described in the previous section. The method for binning new data is identical to that described above except that the rotation matrices and split levels from $D_{old}$ are used rather than being recalculated from the new data set. Step (1) above is replaced with a step which reads in the boundaries of the original data space, rotation matrices, and split values. Step (2) is identical except that the steps (2)b.i, (2)b.iii, and (2)b.iv are skipped and the rotation matrices and split values utilized in the remaining steps are those that were read in new step (1). The procedure is as follows:

(1) Initialization a. Read in the stored values for the template data set that has been binned by the procedure described above. These values are:

i. The boundaries of the data space:

$x_1 = xmin_1, x_1 = xmax_1$, $x_2 = xmin_2, x_2 = xmax_2$,

. . .

$x_p = xmin_p, x_p = xmax_p$ ii. The rotation matrices: $R_n$ for n=1, 2, . . . , $N_T$
iii. The split values: $t_n$ for n=1, 2, . . . , $N_T$ b. Read in data set, $D_{new}$.

Denote the number of events in this data set as m.

c. Set the boundaries for the zero'th resolution level to the values read in at step (1)a.i.

(Note: It is assumed that the coordinates of the new data set span the same range as the template data set.)

d. Set two bin counters, $n_{beg}$ and $n_{end}$, which define the beginning and ending bin numbers for the current resolution level. For the zero'th resolution level, set k=0, $n_{beg}$=1, and $n_{end}$=1.
e. Set a bin counter, b, to b=1.
f. Store the data contained within the boundaries of the current bin in an array, $D_1$=$D_{new}$. The number of data points in $D_1$, is $m_1$=m.

(2) Begin a loop over bins using b as a bin number counter. Continue this loop until the value of b exceeds $N_T$. When b exceeds $N_T$, continue at step (3) below.
  a. Increment the resolution level, k=k+1, and set n=$n_{beg}$.
  b. Begin a loop over bins, n=$n_{beg}$ to $n_{end}$.
    i. Rotate the $m_n$ data points, $D_n$, contained within bin n by the rotation matrix $R_n$. The rotated data is referred to as $D_n'$ and has points described by x'=($x'_1$, $x'_2$, ..., $x'_p$).
    ii. Divide the data points in bin n according to whether their values for $x'_1$ are less than or greater than $t_n$. The split data is stored in two arrays:
      $D_{low}$ contains points, j, such that the values $x^{ij}_1$ are less than or equal to $t_n$.
      $D_{high}$ contains points, j, such that the values $x^{ij}_1$ are greater than $t_n$.
    iii. Increment the bin counter, b, by one: b=b+1. Store data points, $D_{low}$, in bin b: $D_b$=$D_{low}$.
    iv. Increment the bin counter, b, by one: b=b+1. Store data points, $D_{high}$, in bin b: $D_b$=$D_{high}$.
    v. Increment counter n: n=n+1
      If n is less than or equal to $n_{end}$, continue the loop over n at step (2)b.
      Otherwise, proceed with step (2)c.
  c. Replace the current values of $n_{beg}$ and $n_{end}$ as follows: $n_{beg}$=$n_{end}$+1, and $n_{end}$=b.
  d. Continue the loop which began at step (2) above.

(3) Terminate the binning procedure.

Method for Fingerprint Generation

Figure 4:
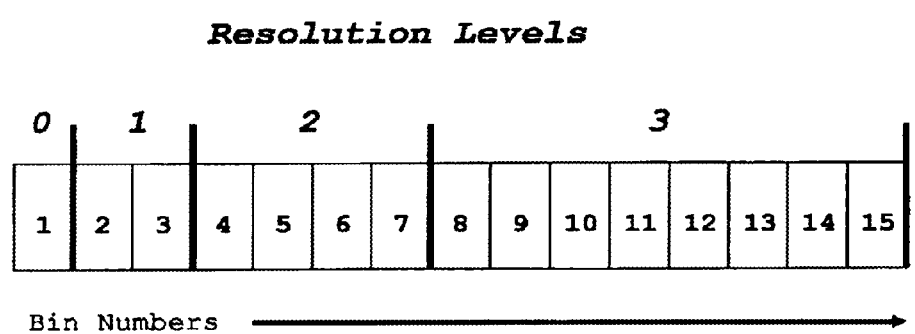
FIG. 4 is a schematic representation of a fingerprint showing the bin numbering and subdivisions corresponding to the different resolution hierarchies. In this example, there are 4 resolution levels. Level 0 has 1 bin that contains the entire data set; level 1 divides the data into two bins; level 2 into 4 bins; and level 3 into 8 bins.

In an embodiment of the invention, the binning procedure described above represents a partitioning of the multidimensional data space into an enumerated set of regions. The number of events contained within each of these regions is nearly identical (for the data set from which bins are determined). The bin boundaries at a particular hierarchical level represent an estimate for the probability density function for the data set at the corresponding level of resolution. In particular, the bins represent regions that have nearly equal probabilities since the event counts are nearly identical in each bin. In order to obtain a fingerprint for a new sample instance relative to an estimation of the probability density function from another instance (referred to here as the "template" instance), one can bin the data from the new sample as described above. A density of events for each bin can be obtained by dividing event counts by the total number of events in the sample. Since the bins are enumerated, a simple one-dimensional representation of the density variations, relative to the template instance, may be obtained by recording the densities for the successive bins in the form of a list. FIG. 4 is a schematic representation of this list showing the subdivisions corresponding to the different resolution hierarchies. This representation is referred to as a "fingerprint" since it distinguishes differing instances. Given a set of instances, a fingerprint for each instance may be obtained by this procedure.

Fingerprints for a Set of Instances Relative to the Probability Density for a Template Instance It is often the case that one would like to describe the differences between each individual instance in a set and a "template" instance which represents the entire set of instances. In one embodiment, a fingerprint representing these differences may be found as follows.
  (1) For a set of M instances, $S_1$, $S_2$, ..., $S_M$, aggregate the events from all of the instances to form a single composite instance denoted as S.
  (2) Find a set of bins for the data in S.
  (3) Bin the data for each instance, $S_i$, i=1, 2, ..., M, using the bins found in step 2.
  (4) Convert the event counts in each bin into an event density by dividing each count by the total number of events in the data set.

The lists of binned event densities for the set of instances, $S_1$, $S_2$, ..., $S_M$, form a set of fingerprints for these data relative to the probability density estimated from the composite data set.

Fingerprints for Classification

In another embodiment of the invention, another variation of fingerprinting is particularly useful for classifying instances. The goal is to emphasize differences between samples belonging to different classes. For classification problems, one typically has a set of training instances for which the class identity is known and a set of test or validation instances for which the class identity is unknown. The training data can be used to construct "template" instances to estimate the probability densities for each class. Using individual instances from a training set, one can obtain statistical measures for the average and degree of variation for each bin. These statistics can be used to convert from event densities to a z-score defined as: $z=(r-r_{AVG})/r_{STD}$ where r is the event density for a bin, $r_{AVG}$ is the average event density for a bin, and $r_{STD}$ is the standard deviation of event densities for a bin. Here, averages and standard deviations are found using all of the training instances from one class. The z-score may be thought of as normalizing event densities by measuring the number of standard deviations from the mean for a given event density. Z-scores can also be calculated for instances that are not part of the training data. These are a normalized measure of event density variations relative to the estimate of the PDF for a given class. A property of z-scores is that within a class, one expects the statistical distribution of z-scores to have an average value of zero and a standard deviation of one (referred to here as a zero-mean, unit-variance distribution). The degree to which the distribution of z-scores for instances outside the class vary from this zero-mean, unit-variance distribution is a measure of the dissimilarity of instances outside of the class to those in the class. The normalization properties of the z-score make it desirable to convert from event densities to z-score in constructing fingerprints for classification since it places all measurements on the same scale.

By way of a non-limiting example, following are the steps used to construct fingerprints for a two class problem. (This procedure easily generalizes to multiple classes.)
  (1) For two classes A and B, obtain composite, template instances for each class. This may be done by aggregating each class's set of training instances. Denote the numbers of instances in classes A and B by, $N_A$ and $N_B$. Denote data for these two composite instances by $S_A$ and $S_B$.
  (2) Calculate the multidimensional, minimum variance equal probability, hierarchical bins as described above for the two data sets $S_A$ and $S_B$.
  (3) Bin the data for each individual instance $S_{Ai}$ of class A relative to the bins found from $S_A$.
    (i=1, 2, ..., $N_A$). Denote the event densities for these bins as $r_{AiA}$.
  (4) Calculate the average and standard deviations for event densities for each bin using the binned data for each $S_{Ai}$ binned relative to $S_A$. Denote this set of averages and standard deviations as $AVG_{AA}$ and $STD_{AA}$. (Note that there will be $N_T$ elements in this set; one for every bin.)

(5) Bin the data for each individual instance $S_{Bj}$ of class B relative to the bins found from $S_A$.

(j=1, 2, ..., $N_B$). Denote the event densities for these bins as $r_{BjA}$.

(6) Bin the data for each individual instance $S_{Ai}$ of class A relative to the bins found from $S_B$.

(i=1, 2, ..., $N_A$). Denote the event densities for these bins as $r_{AiB}$.

(7) Bin the data for each individual instance $S_{Bj}$ of class B relative to the bins found from $S_B$.

(j=1, 2, ..., $N_B$). Denote the event densities for these bins as $r_{BjB}$.

(8) Calculate the average and standard deviations for event densities for each bin using the binned data for each $S_{Bj}$ binned relative to $S_B$. Denote this set of averages and standard deviations as $AVG_{BB}$ and $STD_{BB}$. (Note that there will be $N_T$ elements in this set; one for every bin.)

(9) Bin the data for instances $U_k$ (k=1, 2, ..., $N_U$) whose class is not known (for example test, validation, or unknown instances) relative to $S_A$ and relative to $S_B$. Denote the event densities for these bins as: $r_{UkA}$ and $r_{UkB}$ respectively.

(10) Convert event densities to z-scores as follows:

$Z_{AiA} = (r_{AiA} - AVG_{AA})/STD_{AA}$ for (i=1, 2, ..., $N_A$)

$Z_{AiB} = (r_{AiB} - AVG_{BB})/STD_{BB}$ for (i=1, 2, ..., $N_A$)

$Z_{BjA} = (r_{BjA} - AVG_{AA})/STD_{AA}$ for (j=1, 2, ..., $N_B$)

$Z_{BjB} = (r_{BjB} - AVG_{BB})/STD_{BB}$ for (j=1, 2, ..., $N_B$)

$Z_{UkA} = (r_{UkA} - AVG_{AA})/STD_{AA}$ for (k=1, 2, ..., $N_U$)

$Z_{UkB} = (r_{UkB} - AVG_{BB})/STD_{BB}$ for (k=1, 2, ..., $N_U$)

(11) Construct fingerprints as described above for instances A relative to A using z-scores $Z_{AiA}$. Denote these fingerprints as $f_{AiA}$.

(12) Construct fingerprints as described above for instances A relative to B using z-scores $Z_{AiB}$. Denote these fingerprints as $f_{AiB}$.

(13) Construct fingerprints as described above for instances B relative to A using z-scores $Z_{BjA}$. Denote these fingerprints as $f_{BjA}$.

(14) Construct fingerprints as described above for instances B relative to B using z-scores $Z_{BjB}$. Denote these fingerprints as $f_{BjB}$.

(15) Construct fingerprints as described above for instances U relative to A using z-scores $Z_{UkA}$. Denote these fingerprints as $f_{UkA}$.

(16) Construct fingerprints as described above for instances U relative to B using z-scores $Z_{UkB}$. Denote these fingerprints as $f_{UkB}$.

(17) Construct composite fingerprints for the instances from training class A by concatenating fingerprints $f_{AiA}$ and $f_{AiB}$. Denote these fingerprints as $g_{AiAB}$.

(18) Construct composite fingerprints for the instances from training class B by concatenating fingerprints $f_{BjA}$ and $f_{BjB}$. Denote these fingerprints as $g_{BjAB}$.

(19) Construct composite fingerprint for the instances from unknown class U by concatenating fingerprints $f_{UkA}$ and $f_{UkB}$. Denote these fingerprints as $g_{UkAB}$.

Figure 5:
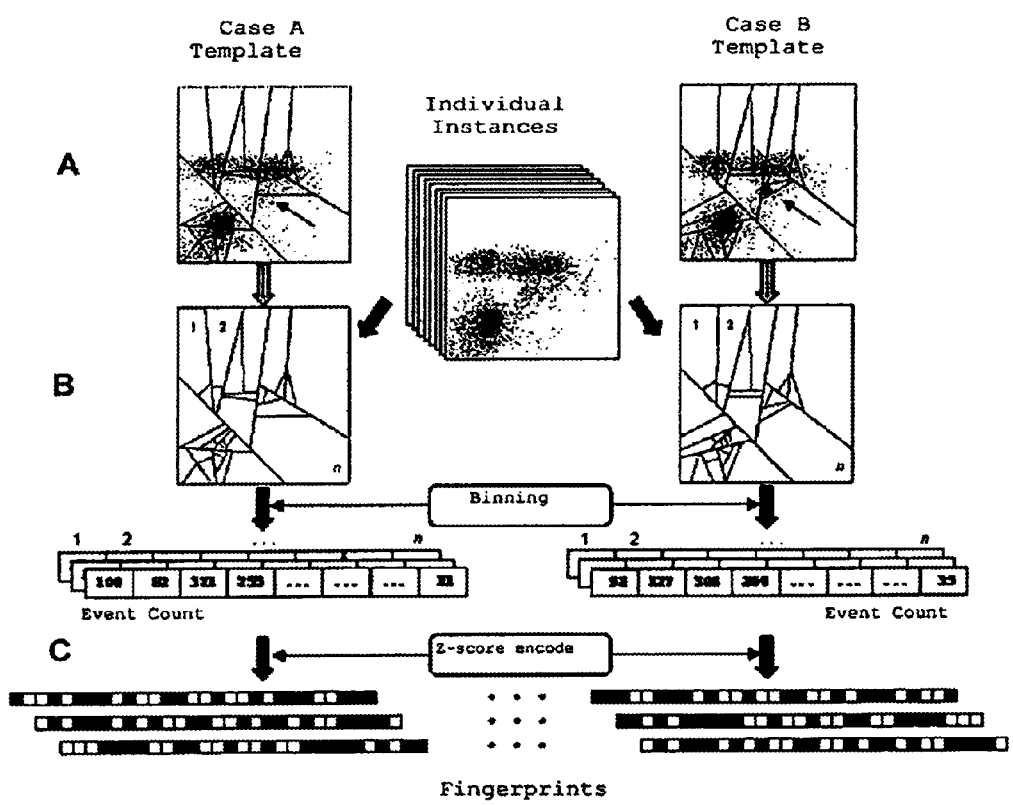
FIG. 5 shows a schematic diagram fingerprint construction according to the invention. A. Hierarchical Binning is performed on aggregates of two classifications of data to create two separate sub-divisions of multidimensional space. (Although this figure depicts the process in 2 dimensions for graphical simplicity, in reality it operates in the full dimensionality of the data). B. Each set of bins is applied to each individual data set. The event count in each of the n bins for each data set is mapped to a 1-dimensional array. C. These arrays of event counts are encoded by assigning z-scores that reflect differences between individual samples and the population event count in each bin. The z-scores are then quantized to form categorical features. In the final step, the categorical features are encoded as binary features to create binary fingerprints.

The sets of fingerprints, $g_{AiAB}$, $g_{BjAB}$, and $g_{UkAB}$ capture the probability density variations of each of the sets of instances, A, B, and U, relative to bins determined from template instances for classes A and B. Since the template for class A is the aggregate of the class A instances, one would expect the portion of the fingerprint corresponding to $f_{AiA}$ to have small z-score values (not much variation from the average) while the portion of the fingerprint $f_{AiB}$ to have larger z-score values since there is less similarity between individual instances from class A and the template probability density function for class B. A corresponding statement can be made regarding fingerprints for class B relative to classes A and B. Test, validation, or unknown instances may be classified by measuring their similarity to the training fingerprints for class A and B. A schematic diagram of the fingerprint process for classification is shown in FIG. 5.

Categorical and Binary Fingerprints

In an embodiment of the invention, a means of determining the similarity of instances is to find patterns that are common to sets of fingerprints. (Moser 2005) Useful forms of fingerprints for pattern discovery are categorical and binary representations. For a categorical representation, the values comprising the elements of the fingerprint may be quantized into some number of discrete categories. For example, this may be accomplished by using a series of numerical thresholds. For a set of thresholds $t_1 < t_2 < \ldots t_M$, assign categorical variable $x_l$ to z-score z if $t_l < z < t_{l+1}$. Categorical fingerprints are obtained by substituting the calculated categorical variable computed from the z-score and thresholds into the list comprising the fingerprint at the location of its corresponding z-score.

Once categorical fingerprints have been obtained, they can be easily transformed to a binary representation by assigning a set of indicator binary variables to each category. For example, if there are 5 categorical values, assign strings of binary digits as follows:

00001 represents categorical variable 1
00010 represents categorical variable 2
00100 represents categorical variable 3
01000 represents categorical variable 4
10000 represents categorical variable 5.

These fingerprints may then be processed by a binary pattern discovery algorithm such as that described in (Moser 2005).

Data Analysis Applications

The present invention is useful for analysis of data in a multitude of settings and applications. As set forth elsewhere herein, the analysis of flow cytometric data has great importance in understanding biological systems and in clinical medicine. In one embodiment, the invention set forth herein has direct applicability to flow cytometric data. In an embodiment, the invention can be used to describe flow cytometric data. In raw form, these data are described as "list-mode" files giving the parameter values for each cell in a sample. These data are often subsequently processed by quadrant analysis, whereby the parameter space is segmented into two regions, or by gating to give the fraction of cells within regions of space that have been delineated by an operator. Because of the limitation of display devices and an inability to visualize multiple dimensions simultaneously, this is most often done as a sequential process whereby sets of gates (or quadrants) are specified in two dimensions at a time. The invention also provides a method of describing flow cytometric data as set of multidimensional regions (covering the entire space at multiple resolutions) that have been automatically determined through the presently-disclosed Multidimensional Minimum Variance Equal Probability Hierarchical Binning procedure. Thus, this invention has general utility to the field of Flow Cytometry.

In another embodiment, the invention is used in quality control processes in the field of Flow Cytometry. An important task in flow cytometry is insuring that instruments are working correctly and results are reproducible. Often, flow cytometric analysis is carried out on multiple samples from one patient. For example, several tubes of blood may be drawn and each is stained with different antibody panels. However, these antibody panels often overlap. For example, in a five tube analysis, each of the five tubes may include antibodies for CD45 which is useful in identifying lymphocytes. Additionally, data is almost always acquired for forward and side scatter. Thus, repeated measurements of several parameters from multiple samples for the same patient are available. In an aspect, the invention can be used to find fingerprints representing these repeated measurements. The similarity of these fingerprints across a set of samples from the same patient can be used to measure the reproducibility, and thus quality, of the cytometric data.

Figure 2:
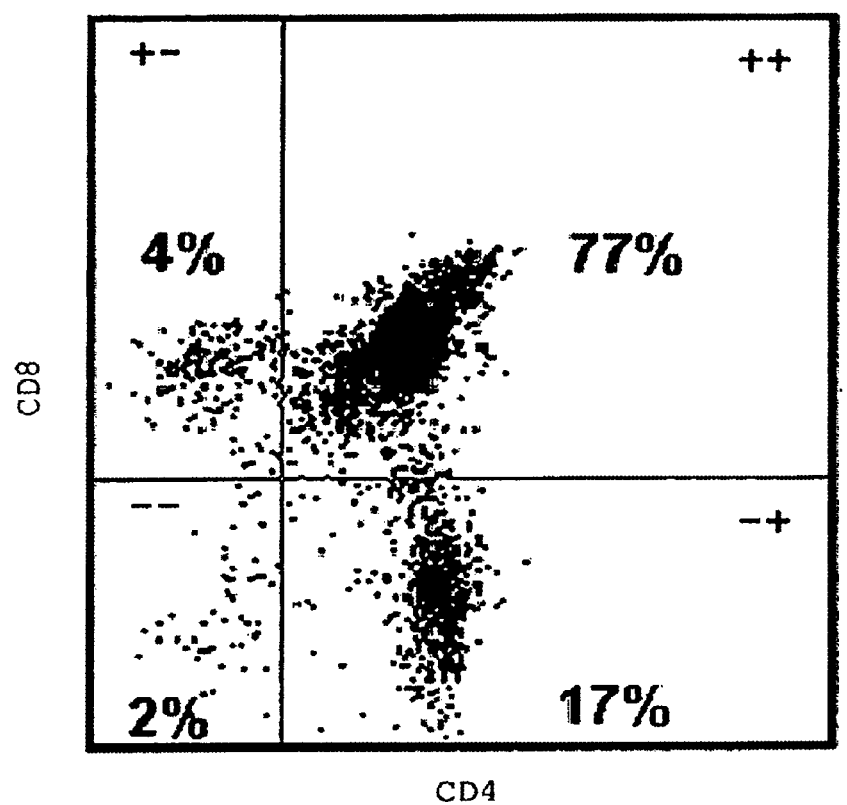
FIG. 2 shows an 2-dimensional flow cytometry data for T-lymphocytes, an example of quadrant analysis for flow cytometric data. This figure illustrates light intensities for fluorophores conjugated with antibody CD8 versus those conjugated with antibody CD4. The space is divided into positives and negatives in CD4 and CD8. Percentages of positive-positive, positive-negative, negative-positive, and negative-negative are shown. (From Purdue University Cytometry Laboratory web-site, (dot)http:(two forward slashes)www(dot)cyto(dot)purdue.edu).

Flow cytometry has a broad range of uses in medicine including clinical measurements for disease diagnosis, prognosis, classification, and progression. The present invention has direct applicability to the use of flow cytometric data for these applications. Currently, flow cytometry is most useful in clinical medicine when optimized antibody panels are available. In this case, cell populations can be distinguished by quadrant analysis or sequential gating as shown, for example in FIG. 2 for T-lymphocyte measurements related to HIV infection. However, these methods of analysis do not work well when cell antigens and specific antibodies are not well characterized, cell surface markers change with time, or distributions of intensity levels from cytometric measurements are complex and overlapping. The present invention provides a means of representing and utilizing flow cytometric data for clinical medicine in these situations. Utilizing data from known populations (e.g. diseased versus non-diseased individuals), fingerprints can be developed, using the methods described in this invention, that can be used to classify patients. Thus, the present invention has both general and broad application to problems of clinical medicine including diagnostics, prognostics, disease progression and disease classification.

It will also be understood by the skilled artisan, when armed with the present disclosure, that the present invention also has broader applicability. Multiple and varied medical-related applications have been set forth herein. However, the methods and apparatuses of the invention can also be applied to any type of data that involves measurements that can be represented in a multidimensional space. By way of a non-limiting example, the invention can be used for data analysis in astronomy, in which the distribution of stars in a 3-dimensional space can be represented using the invention. Other non-limiting examples of applications of the present invention include classification, processing and analysis of banking data (e.g., characterization of credit risk in terms of multiple dimensions, such as demographics, financial resources, etc., as well as to classify potential credit card customers). Therefore, the skilled artisan will understand, based on the disclosure set forth herein, that the methods and apparatuses of the invention can be used in any situation where data are described by multiple parameters that can be numerically quantified.

Additional Embodiments of the Invention

In another embodiment, the invention includes a method of representing data at multiple resolutions, the data being described by a multidimensional space containing multiple events consisting of measurements of multiple parameters; the method comprising:

a) describing said data as a distribution of events in a multidimensional space where each coordinate axis of the space has a unique correspondence to one of the measured parameters;

b) determining the boundaries of the multidimensional space as the minimum and maximum possible values for the parameter corresponding to each axis;

c) specifying the number of regions, referred to as bins, into which the data space is to be divided for the highest resolution representation of the data space;

d) determining the number which is an exact power of two closest to the number of high resolution bins specified in the previous step;

e) determining the total number of resolution levels as the number determined in the previous step plus one;

f) enumerating the resolution levels as a sequence of integers starting at zero and ending at the total number of resolution levels minus one;

g) determining the number of bins at each resolution level as two raised to the power of the integer specified in the enumeration for the corresponding resolution level;

h) determining the total number of bins as one less than two raised to the power of the total number of resolution levels; and i) enumerating the totality of all bins starting at the lowest resolution level, proceeding to the next higher resolution level, and continuing to the highest resolution level; this specification of the order of bins forming an enumerated, hierarchical, multiresolution representation of the data.

In another embodiment, a method further comprises:

a) recording the values defining the boundaries of the data space on a storage device; and b) recording the value for the total number of bins into which the data space is to be divided on a storage device.

In another embodiment, a method further comprises:

a) forming a bin of lowest resolution encompassing the complete data space and comprising all of the data within the data set; and b) beginning with the lowest resolution, iterating over each level of resolution, subdividing each bin at a given resolution to form two bins at a higher resolution, continuing this subdivision until the desired number of bins is obtained.

In another embodiment, a method further comprises:

a) in the process of subdividing the data from each bin into finer resolutions bins, determining the direction of maximum variance of the data contained within the given bin;

b) rotating the coordinates of the data space in the direction of maximum variance in such a way that the first axis of the rotated coordinate systems is parallel to the direction of maximum variance;

c) determining the median value of the first coordinate in the rotated coordinate system for the collection of data comprising the bin;

d) splitting the data comprising the current bin into two bins at the next hierarchical resolution level, the first portion being comprised of events whose first coordinate value is less than or equal to the median, the second portion being comprised of events whose first coordinate value is greater than the median; and e) recording the rotation matrix and median value (split value) associated with the current bin to a storage device;

The invention also includes a method of partitioning multidimensional data from one data set into regions defined by the application of the binning procedure, as described elsewhere herein, to a different data set; the method comprising:

a) reading the data space boundaries, set of rotation matrices, and set of split values for each bin to be formed in the binning process from a storage device;

b) forming a bin of lowest resolution encompassing the complete data space and comprising all of the data within the data set; and c) beginning with the lowest resolution, iterating over each level of resolution, subdividing each bin at a given resolution to form two bins at a higher resolution, continuing this subdivision until the desired number of bins is obtained.

In another embodiment, a method further comprises:

a) in the process of subdividing the data within each bin into finer resolutions bins, rotate the data space by applying the rotation matrix corresponding to the current bin; and b) utilizing the split value for the current bin, splitting the data comprising the current bin into two bins at the next hierarchical resolution level, the first portion being comprised of events whose first coordinate value is less than or equal to the median, the second portion being comprised of events whose first coordinate value is greater than the median.

The invention also includes a method of determining the hyperplane boundaries of bins found through the application of the binning procedure as described elsewhere herein; the method comprising:

a) reading the data space boundaries, set of rotation matrices, and set of split values for each bin whose hyperplane boundaries are to be determined from a storage device;

b) specifying a rotation matrix of unit diagonal and zero off diagonal elements as the parent of the lowest resolution bin;

c) starting with the bin of lowest resolution, defining the hyperplane boundaries as the set of boundaries read in from the storage device;

d) beginning with the lowest resolution, iterating over each level of resolution, intersecting the hyperplane boundaries of the current bin with the hyperplane boundary utilized to split the current bin into its two children bins of higher resolution; and e) recording the two sets of boundaries determined by this intersection as the hyperplane boundaries of the two children bin.

In another embodiment, a method further comprises:

a) in the process of iterating over resolution levels to find bin boundaries, multiplying the rotation matrix for a bin by the rotation matrix of its parent bin;

b) associating this product matrix with the current bin to be used as a parent bin in the next step in the iteration;

c) constructing a direction vector from the elements of the first column of the product matrix computed in the previous step;

d) finding the hyperplane perpendicular to the direction vector constructed in the previous step that passes through the split value for the current bin; and e) identifying the hyperplane found in the previous step as the boundary utilized to split the current bin into its two children bins of higher resolution.

The invention also includes a method of determining one-dimensional lists of numbers comprising fingerprints for a set of instances relative to the representation of a multidimensional data set that has been processed by the binning procedure as described in detail elsewhere herein; the method comprising:

a) forming a template instance by combining the events from a set of instances into a single data set;

b) determining a set of bins representing the template instance as described elsewhere herein; and c) binning the data comprising each instance of the set of instances used to form the template instances, or each instance of some other set of instances.

In another embodiment, a method further comprises:

a) for all of the instances in the set of instances, calculating an event density for each bin by dividing the number of events in each bin by the total number of events comprising the instance; and b) optionally performing other mathematical transformations on the values of event densities.

In another embodiment, a method further comprises:

a) enumerating the bins in order of hierarchies of increasing resolution, and within a resolution level, in the order in which the bins were determined by the methods described herein; and b) creating a list of the numerical values associated with each bin in the enumerated order found in the preceding step.

In another embodiment, a method further comprises the step of recording the list of numbers on a storage device.

The invention also includes a method of determining one-dimensional lists of numbers comprising fingerprints for sets of instances relative to the representations of two or more multidimensional data sets that have been processed by the binning procedure described elsewhere herein; the method comprising:

a) specifying two or more sets of instances, each set comprising a class of data sets;

b) for each class, forming a template instance for that class by combining the events from the set of instances comprising the class into single data set; and c) for each class, using the method described elsewhere herein to determine a set of bins representing each template instance.

In another embodiment, a method further comprises:

a) for each class, for the instances comprising that class, using the method described herein to bin the data comprising each instance of that class relative to template instance for that class;

b) for the binned representations of instances found in the previous step, using the methods described herein to form fingerprints for each instance; and c) for each class, for the fingerprints for instances comprising the class, for each feature in the fingerprint, calculating the average and standard deviation of each feature, there now being an average and standard deviation associated with each bin for each class.

In another embodiment, a method further comprises:

a) for each class, for the instances not comprising that class, using the method described herein to bin the data comprising each instance not of that class relative to template instance for that class; and b) for the binned representations of instances found in the previous step, using the methods described herein to form fingerprints for each instance.

In another embodiment, a method further comprises:

a) for each class, for each fingerprint constructed as described herein, calculating a z-score for each feature in the fingerprint by subtracting the average associated with the class as described herein for the corresponding feature and then dividing that result by the standard deviation associated with the class as described herein for the corresponding feature, this result giving a set of fingerprints for each instance, the number of elements of that set being equal to the number of classes.

In another embodiment, a method further comprises:

a) for each instance, combining the set of fingerprints, constructed using the method described herein, by concatenating the lists of elements in each fingerprint, thereby forming a single fingerprint for each instance which contains that instance's z-score calculated relative to every class; and b) optionally performing other mathematical transformations on every feature of the fingerprints.

The invention further includes a method of forming a categorical fingerprint from a fingerprint created by the methods described elsewhere herein; the method comprising:

a) defining a many-to-one mapping of continuous valued numbers into a discrete set of values, those values being integers or some other discrete label, the method of mapping being a mathematical transform such as quantization, a transform based on a machine learning method, or any other transform capable of a many-to-one mapping;

b) applying the mapping described in the previous step to each feature of the fingerprint; and c) creating a list of the mapped features thereby forming a fingerprint consisting of categorical features.

The invention also includes a method of forming a binary fingerprint from a fingerprint created by the method described elsewhere herein; the method comprising:

a) specifying the number of non-redundant, discrete features that comprise a categorical fingerprint;

b) assigning a integer ordinal to each categorical feature;

c) creating a mapping of each categorical feature to a string of binary digits, the number of elements in the string being equal to the number of categorical features, by setting all digits in the string to zero excepting the element whose position in the string corresponds to the ordinal of the categorical feature, that element being set to one;

d) applying the mapping described in the previous step to each feature of the categorical fingerprint; and creating a list of the mapped features thereby forming a fingerprint consisting of binary features.

Apparatuses

In an aspect of the invention, each of the methods described herein may be implemented as a program or programs of instructions executed by computer. In a typical realization, such a program or programs of instructions can be saved on a mass storage device, such as for example a hard disk drive, a floppy disk drive, or a magnetic tape storage device, or even a plurality of such devices. Thus the program or programs of instructions may be read in and executed by one or more machines, either serially or in parallel, depending on the data in consideration. It will be understood that the novelty and utility of both the methods and their implementations are not dependent on any particular embodiment of computer(s) or mass storage device(s).

Figure 6:
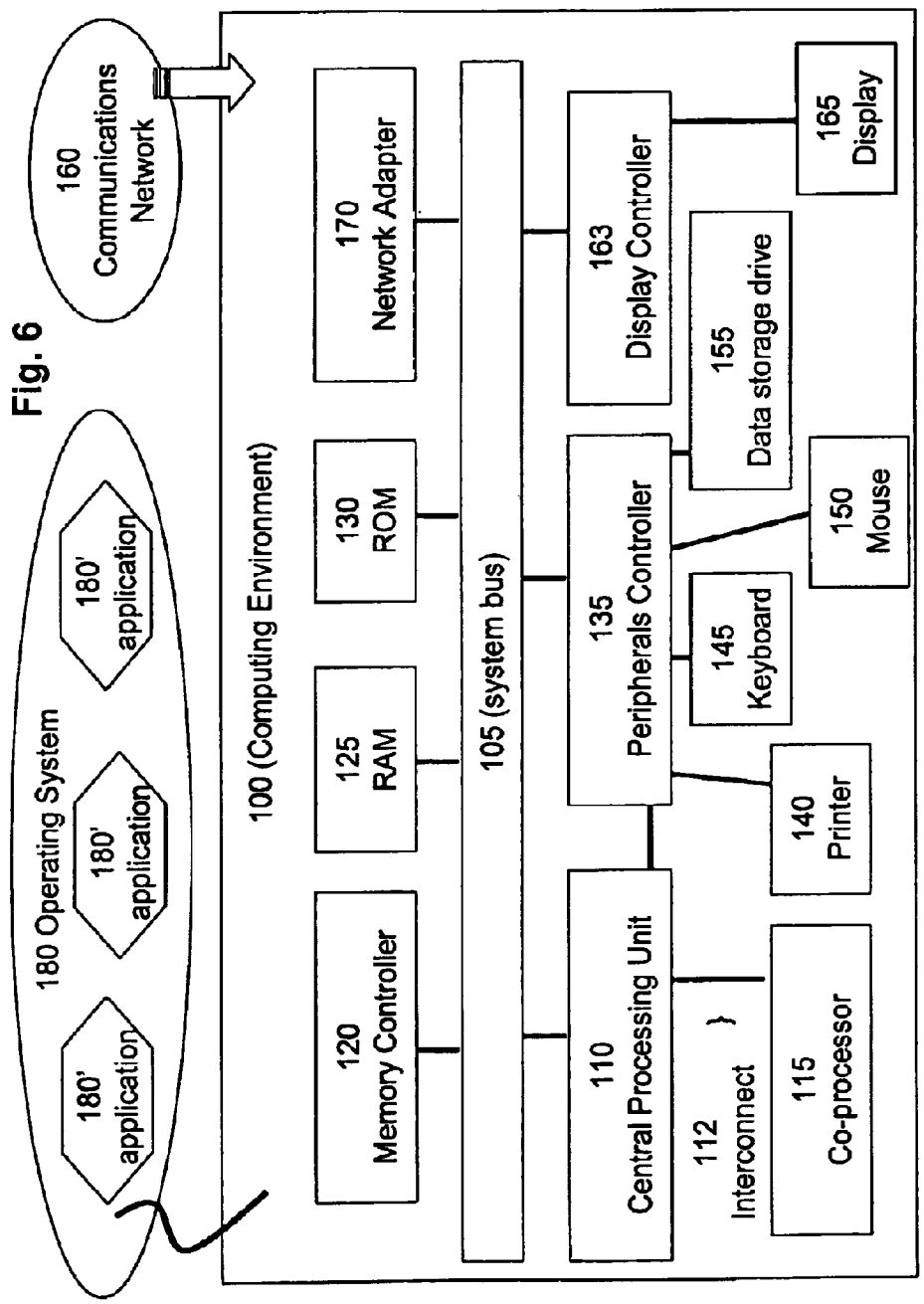
FIG. 6 depicts an exemplary computing system in accordance with herein described system and methods.

FIG. 6 depicts an exemplary computing system 100 in accordance with herein described system and methods. Computing system 100 is capable of executing a variety of operating systems 180 and computing applications 180' (e.g. web browser and mobile desktop environment) operable on operating system 180. Exemplary computing system 100 is controlled primarily by computer readable instructions, which may be in the form of software, where and how such software is stored or accessed. Such software may be executed within central processing unit (CPU) 110 to cause data processing system 100 to do work. In many known computer servers, workstations and personal computers central processing unit 110 is implemented by micro-electronic chips CPUs called microprocessors. Coprocessor 115 is an optional processor, distinct from main CPU 110, that performs additional functions or assists CPU 110. CPU 110 may be connected to co-processor 115 through interconnect 112. One common type of coprocessor is the floating-point coprocessor, also called a numeric or math coprocessor, which is designed to perform numeric calculations faster and better than general-purpose CPU 110.

It is appreciated that although an illustrative computing environment is shown to comprise a single CPU 110 that such description is merely illustrative as computing environment 100 may comprise a number of CPUs 110. Additionally computing environment 100 may exploit the resources of remote CPUs (not shown) through communications network 160 or some other data communications means (not shown).

In operation, CPU 110 fetches, decodes, and executes instructions, and transfers information to and from other resources via the computer's main data-transfer path, system bus 105. Such a system bus connects the components in computing system 100 and defines the medium for data exchange. System bus 105 typically includes data lines for sending data, address lines for sending addresses, and control lines for sending interrupts and for operating the system bus. An example of such a system bus is the PCI (Peripheral Component Interconnect) bus. Some of today's advanced busses provide a function called bus arbitration that regulates access to the bus by extension cards, controllers, and CPU 110. Devices that attach to these busses and arbitrate to take over the bus are called bus masters. Bus master support also allows multiprocessor configurations of the busses to be created by the addition of bus master adapters containing a processor and its support chips.

Memory devices coupled to system bus 105 include random access memory (RAM) 125 and read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode can normally access only memory mapped by its own process virtual address space; it cannot access memory within another process's virtual address space unless memory sharing between the processes has been set up.

In addition, computing system 100 may contain peripherals controller 135 responsible for communicating instructions from CPU 110 to peripherals, such as, printer 140, keyboard 145, mouse 150, and data storage drive 155.

Display 165, which is controlled by display controller 163, is used to display visual output generated by computing system 100. Such visual output may include text, graphics, animated graphics, and video. Display 165 may be implemented with a CRT-based video display, an LCD-based flat-panel display, gas plasma-based flat-panel display, a touch-panel, or other display forms. Display controller 163 includes electronic components required to generate a video signal that is sent to display 165.

Further, computing system 100 may contain network adaptor 170 which may be used to connect computing system 100 to an external communication network 160. Communications network 160 may provide computer users with means of communicating and transferring software and information electronically. Additionally, communications network 160 may provide distributed processing, which involves several computers and the sharing of workloads or cooperative efforts in performing a task. It will be appreciated that the network connections shown are exemplary and other means of establishing a communications link between the computers may be used.

It is appreciated that exemplary computer system 100 is merely illustrative of a computing environment in which the herein described apparatus and methods may operate and does not limit the implementation of the herein described apparatus and methods in computing environments having differing components and configurations as the inventive concepts described herein may be implemented in various computing environments having various components and configurations.

Figure 7:
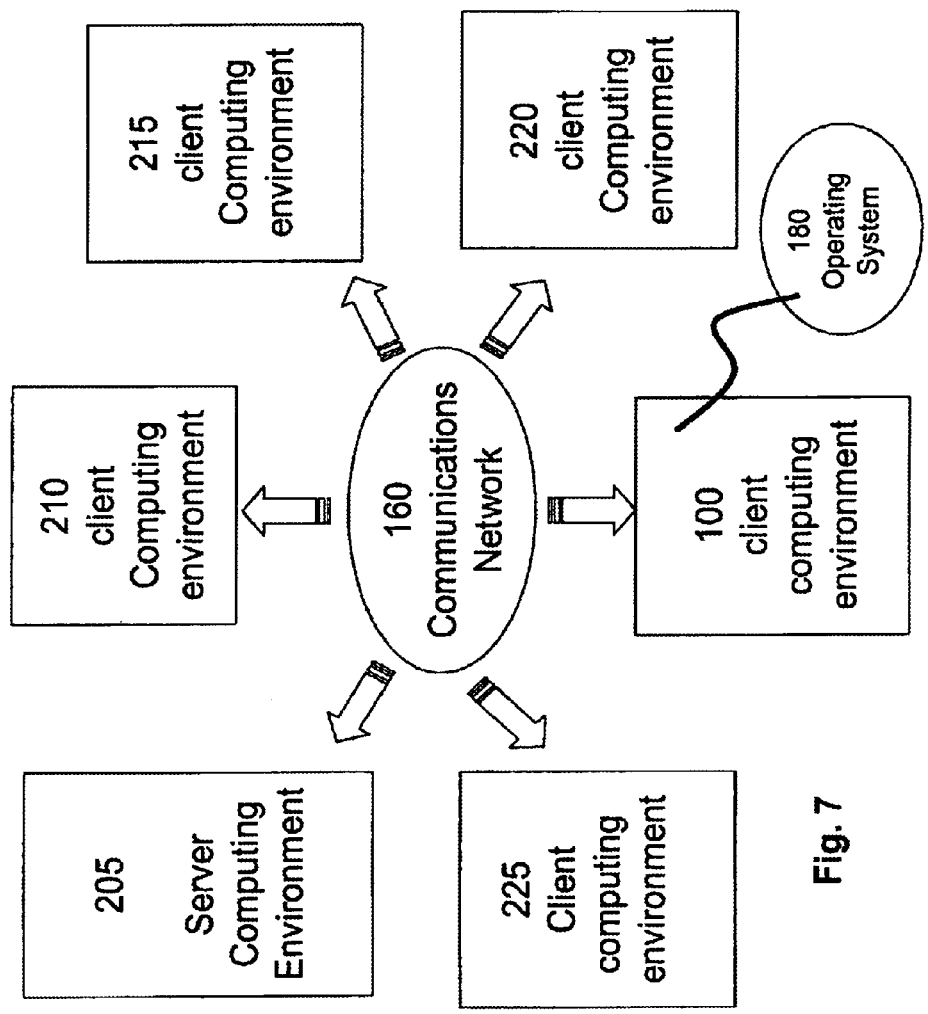
FIG. 7 illustrates an exemplary illustrative networked computing environment, with a server in communication with client computers via a communications network, in which the herein described apparatus and methods may be employed.

Illustrative Computer Network Environment:

Computing system 100, described above, can be deployed as part of a computer network. In general, the above description for computing environments applies to both server computers and client computers deployed in a network environment. FIG. 7 illustrates an exemplary illustrative networked computing environment 200, with a server in communication with client computers via a communications network, in which the herein described apparatus and methods may be employed. Server 205 may be interconnected via a communications network 160 (which may be either of, or a combination of a fixed-wire or wireless LAN, WAN, intranet, extranet, peer-to-peer network, the Internet, or other communications network) with a number of client computing environments such as tablet personal computer 210, mobile telephone 215, telephone 220, personal computer 100, and personal digital assistance 225. Additionally, the herein described apparatus and methods may cooperate with automotive computing environments (not shown), consumer electronic computing environments (not shown), and building automated control computing environments (not shown) via communications network 160. In a network environment in which the communications network 160 is the Internet, for example, server 205 can be dedicated computing environment servers operable to process and communicate web services to and from client computing environments 100, 210, 215, 220, and 225 via any of a number of known protocols, such as, hypertext transfer protocol (HTTP), file transfer protocol (FTP), simple object access protocol (SOAP), or wireless application protocol (WAP). Each client computing environment 100, 210, 215, 220, and 225 can be equipped with browser operating system 180 operable to support one or more computing applications such as a web browser (not shown), or a mobile desktop environment (not shown) to gain access to server computing environment 205.

In operation, a user (not shown) may interact with a computing application running on a client computing environments to obtain desired data and/or computing applications. The data and/or computing applications may be stored on server computing environment 205 and communicated to cooperating users through client computing environments 100, 210, 215, 220, and 225, over exemplary communications network 160. A participating user may request access to specific data and applications housed in whole or in part on server computing environment 205. The applications and/or data may be communicated between client computing environments 100, 210, 215, 220, and 220 and server computing environments for processing and storage. Server computing environment 205 may host computing applications, processes and applets for the generation, authentication, encryption, and communication of web services and may cooperate with other server computing environments (not shown), third party service providers (not shown), network attached storage (NAS) and storage area networks (SAN).

Thus, the apparatus and methods described herein can be utilized in a computer network environment having client computing environments for accessing and interacting with the network and a server computing environment for interacting with client computing environments. However, the apparatus and methods providing the mobility device platform can be implemented with a variety of network-based architectures, and thus should not be limited to the example shown. The herein described apparatus and methods will now be described in more detail with reference to a presently illustrative implementation.

The herein described apparatus and methods provide a mobility device. It is understood, however, that the invention is susceptible to various modifications and alternative constructions. There is no intention to limit the invention to the specific constructions described herein. On the contrary, the herein described apparatus and methods are intended to cover all modifications, alternative constructions, and equivalents falling within the scope and spirit of the herein described apparatus and methods.

It should also be noted that the herein described apparatus and methods may be implemented in a variety of computer environments (including both non-wireless and wireless computer environments), partial computing environments, and real world environments. The various techniques described herein may be implemented in hardware or software, or a combination of both. Preferably, the techniques are implemented in computing environments maintaining programmable computers that include a processor, a storage medium readable by the processor (including volatile and non-volatile memory and/or storage elements), at least one input device, and at least one output device. Computing hardware logic cooperating with various instructions sets are applied to data to perform the functions described above and to generate output information. The output information is applied to one or more output devices. Programs used by the exemplary computing hardware may be preferably implemented in various programming languages, including high level procedural or object oriented programming language to communicate with a computer system. Illustratively the herein described apparatus and methods may be implemented in assembly or machine language, if desired. In any case, the language may be a compiled or interpreted language. Each such computer program is preferably stored on a storage medium or device (e.g., ROM or magnetic disk) that is readable by a general or special purpose programmable computer for configuring and operating the computer when the storage medium or device is read by the computer to perform the procedures described above. The apparatus may also be considered to be implemented as a computer-readable storage medium, configured with a computer program, where the storage medium so configured causes a computer to operate in a specific and predefined manner.

Although an exemplary implementations of the herein described apparatus and methods have been described in detail above, those skilled in the art will readily appreciate that many additional modifications are possible in the exemplary embodiments without materially departing from the novel teachings and advantages of the herein described apparatus and methods. Accordingly, these and all such modifications are intended to be included within the scope of this herein described apparatus and methods. The invention may be better defined by the following exemplary claims.

Those skilled in the art, having the benefits of the teachings of the present invention as hereinabove set forth, may effect numerous modifications thereto. Such modifications are to be construed as lying within the contemplation of the present invention, as defined by the claims herein set forth.

REFERENCES CITED

U.S. Patent Documents

Moser, A. R., et al., 2005, "Method and apparatus for discovering patterns in binary or categorical data," US Patent Application 20050143928.

OTHER PUBLICATIONS

Johnson, R. L., 1993, "Flow cytometry. From research to clinical laboratory applications," *Clin Lab Med*, 13, 831-52.

Jennings C. D. and Foon, K. A., 1997, "Recent Advances in Flow Cytometry: Application to the Diagnostics of hematologic Malignancy," *Blood* 90, 2863-92.

Roederer, M., et al., 2001, "Probability Binning Comparison: A Metric for Quantitating Univariate Distribution Differences," *Cytometry* 45, 37-46.

Roederer, M., et al., 2001, "Probability Binning Comparison: A Metric for Quantitating Multivariate Distribution Differences," *Cytometry* 45, 47-55.

O'Connel M. J., 1974, "Search Program for Significant Variables," *Comp. Phys. Comm.* 8, 49-55.

Golub, G. H. and Van Loan, C. F., 1996, "The Singular Value Decomposition" and "Unitary Matrices" in *Matrix Computations, 3rd ed*. Baltimore, Md.: Johns Hopkins University Press, 70-71 and 73.

We claim:

1. A computer-implemented method of generating a vector of values comprising a multi-resolution characterization of flow cytometry data, the method comprising:
    identifying, at a server comprising a memory and a processor, flow data comprising events that describe a quantity of at least a first antibody in an individual cell, wherein the quantity is identified using flow cytometry;
    generating a vector of values that characterizes the flow data responsive to iteratively identifying a series of hyperplanes used to segregate the flow data into subsets, wherein at each iteration a hyperplane is independently identified based on a subset of the flow data;
       identifying the hyperplane responsive to determining a direction of the maximum variance of the subset of the flow data;
       generating a rotated subset of data responsive to rotating the co-ordinates of the subset of the flow data in the direction of the hyperplane;
    determining a first value of the rotated subset of the flow data;
    splitting the rotated subset of the flow data into two subsets of data according to the first value;
       storing the vector of values in the memory; and
       uniquely identifying the flow data based on the vector of values.

2. The method of claim 1, wherein generating the vector of values that characterizes the flow data comprises storing data that represents the hyperplane in the vector of values.

3. The method of claim 1, wherein generating the vector of values that characterizes the flow data comprises storing the first value in the vector of values.

4. The method of claim 1, further comprising:
    aggregating the flow data associated with a plurality of samples, wherein the plurality of samples are associated with a class; and
    generating a template vector of values based on the aggregate flow data according to the method of claim 1, wherein the template vector of values represents the class.

5. The method of claim 4, further comprising:
    generating a first vector of values based on the flow data associated with a sample; and
    generating a fingerprint for the first vector of values based on the template vector of values.

6. The method of claim 5, wherein generating a fingerprint for the first vector of values based on the template vector of values comprises:
    generating a score that represents a value in the vector of values relative to a probability density associated with the template vector of values.

7. The method of claim 5, wherein the fingerprint is a binary fingerprint.

8. The method of claim 5, wherein the fingerprint is a categorical fingerprint.

9. The method of claim 4, further comprising:
    generating a first template vector, wherein the first template vector represents a first class;
    generating a second template vector, wherein the second template vector represents a second class; and
    determining, based on the first template vector and the second template vector, a set of values that uniquely identify the first class and a set of values that uniquely identify the second class.

10. A computer-implemented method of classifying flow cytometry data, the method comprising:
    identifying, at a server comprising a memory and a processor, flow data comprising events that describe a quantity of at least a first antibody in an individual cell, wherein the quantity is identified using flow cytometry;
    generating a vector of values that characterizes the flow data responsive to iteratively identifying a series of hyperplanes used to segregate the flow data into subsets, wherein at each iteration a hyperplane is identified based on the direction of the maximum variance of a subset of the flow data;
       generating a rotated subset of data responsive to rotating the co-ordinates of the subset of the flow data in the direction of the hyperplane;
    determining a first value of the rotated subset of the flow data;
       splitting the rotated subset of the flow data into two subsets of data according to the first value;
    storing the vector of values in the memory; and
    determining whether the flow data belongs to a class based on the vector of values and a template vector that represents the class.

11. The method of claim 10, wherein the template vector is generated responsive to:
    generating a plurality of vectors of values based on the flow data derived from samples associated with the class; and
    generating the template vector that represents the class responsive to combining the plurality of vectors.

12. The method of claim 10, wherein the template vector represents a class of reproducible data and the step of determining whether the flow data belongs to the class comprises determining a quality of the flow data.

13. The method of claim 10, wherein the template vector represents a class of samples associated with a disease state.

14. The method of claim 13, wherein the step of determining whether the flow data belongs to the class comprises determining a diagnosis associated with an individual.

15. The method of claim 13, wherein the step of determining whether the flow data belongs to the class comprises determining a prognosis associated with an individual.

16. The method of claim 13, wherein the step of determining whether the flow data belongs to the class comprises determining a stage of disease progression associated with an individual.

17. A computer-implemented method of generating a vector of values comprising a multi-resolution characterization of flow cytometry data, the method comprising:

identifying, at a server comprising a memory and a processor, flow data comprising events that describe a quantity of at least a first antibody in an individual cell, wherein the quantity is identified using flow cytometry;

generating a vector of values that characterizes the flow data responsive to iteratively identifying a series of hyperplanes used to segregate the flow data into finer-resolution subsets, wherein at each iteration a hyperplane is independently identified based on a finer-resolution subset of the flow data;

identifying the hyperplane responsive to determining a direction of the maximum variance of the subset of the flow data;

generating a rotated subset of data responsive to rotating the co-ordinates of the subset of the flow data in the direction of the hyperplane;

determining a first median value of the rotated subset of the flow data;

splitting the rotated subset of the flow data into two subsets of data according to the first median value;

storing the vector of values in the memory; and uniquely identifying the flow data based on the vector of values.

* * * * *